United States Patent [19]

Moses

[11] 4,112,933
[45] Sep. 12, 1978

[54] LARYNGOSCOPE OF THE STRAIGHT BLADE TYPE

[76] Inventor: John A. Moses, 30 Kalan Cir., Fairfield, Conn. 06430

[21] Appl. No.: 761,371

[22] Filed: Jan. 21, 1977

[51] Int. Cl.² .............................................. A61B 1/06
[52] U.S. Cl. ...................................... 128/11; 128/15; 128/13
[58] Field of Search .................................. 128/10–13, 128/15, 16

[56] References Cited
U.S. PATENT DOCUMENTS 2,354,471 7/1944 Macintosh ............................... 128/10
3,856,001 12/1974 Phillips .................................... 128/11

*Primary Examiner*—Robert W. Michell
*Assistant Examiner*—Henry S. Layton
*Attorney, Agent, or Firm*—Arthur T. Fattibene

[57] ABSTRACT

This disclosure is directed to an improved laryngoscope blade of the straight blade type, which includes an essentially straight blade portion having a arcuate cross-section and which has connected to a longitudinal edge of the arcuate blade portion an outwardly flared flange so as to reduce the overall height of the blade while maximizing the exposure or vision through the blade to the larynx.

10 Claims, 8 Drawing Figures

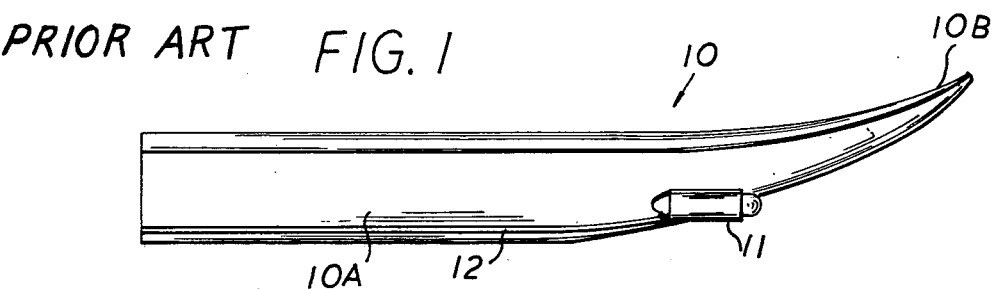
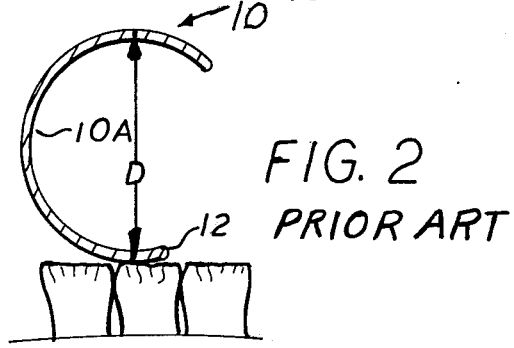
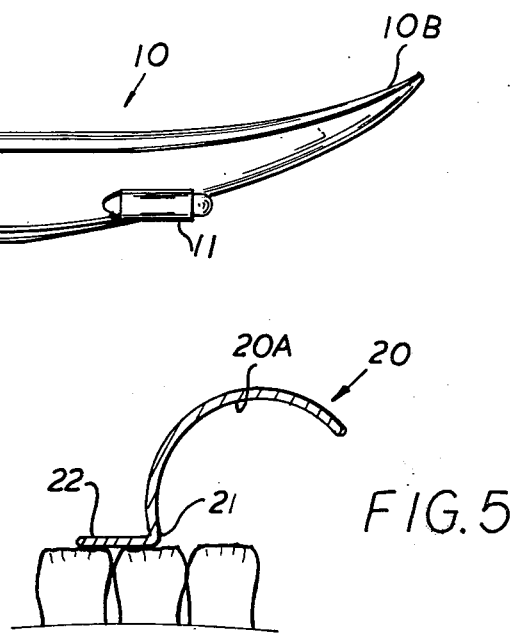
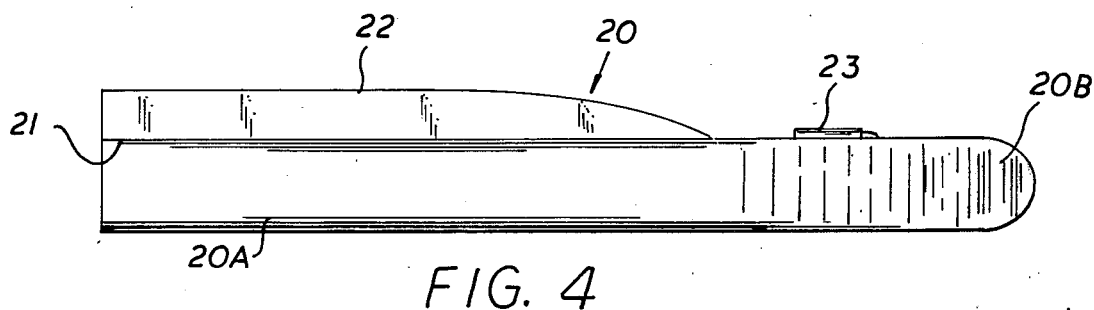
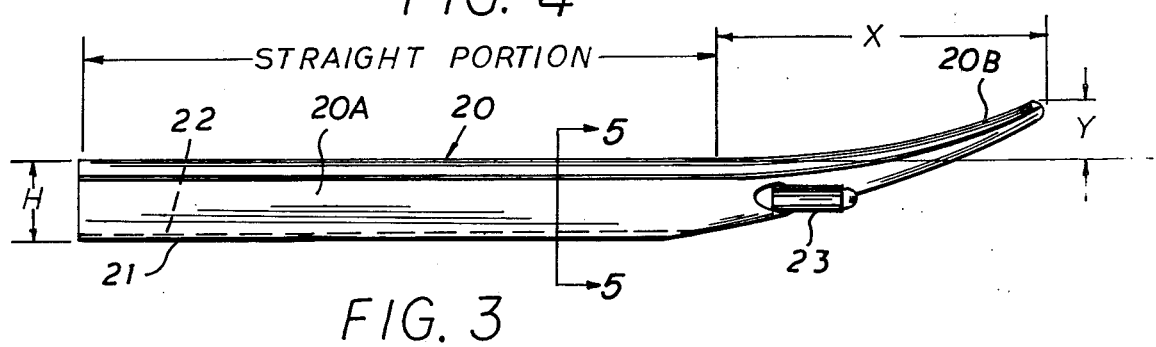

LARYNGOSCOPE OF THE STRAIGHT BLADE TYPE

RELATED APPLICATION

This application relates to a co-pending application Ser. No. 596,356 filed July 16, 1975 for Laryngoscope, now abandoned; in that both applications are directed to Laryngoscope devices each with a specific blade shape particularly when viewed in cross-section.

BACKGROUND OF THE INVENTION

Laryngoscopes are used by doctors and surgeons for viewing the larynx and for endrotracheal intubation. Visualization of the larynx is therefore necessary for passing a tube through the larynx into the trachea. Such endotracheal intubation is usually employed in the administration of anesthesia for the passage of anesthetic gases, vapors and oxygen. Also, the tube helps to keep the airway open and prohibits the patient's tongue from falling down and obstructing the air passage. The tube is also helpful for the anesthesiologist to ventilate the patient manually or mechanically. Endotracheal intubation is also useful in resuscitating patients from cardiac arrest and other emergencies. Therefore, exposure of the larynx with the aid of a laryngoscope is necessary for most endotracheal intubation.

PRIOR ART CONSTRUCTION

A laryngoscope, as generally used in anethesiology, comprises a handle portion containing batteries to provide the source of electrical energy for effecting illumination and a laryngoscope blade hingedly connected to the handle. There are known two general types of laryngoscopes blades; viz., the curve type often referred to as a Macintosh blade as described in U.S. Pat. No. 2,354,471 and the straight type as described in U.S. Pat. No. 2,433,705 and U.S. Pat. No. 2,289,226.

The technique of using the so-called curved type blade and straight type blade differ. With the so-called curved blade the inner end or tip is inserted in the groove formed between the tongue and the epiglottis. With the curved blade so positioned and by lifting up the base of the tongue, the epiglottis is indirectly lifted with it. A characteristic of the curved blade is that the entire length of the blade is curvilinear.

In the so-called straight blade, the blade is essentially straight throughout. More recently the straight blades have been formed with the free end or tip being slightly curved which helps to pick up the epiglottis. The technique in using the straight blade laryngoscope is to place the inner or tip end under the epiglottis and lifting the epiglottis up directly with the tip end of the blade to expose the larynx.

The earliest known straight blades are frequently referred to as Jackson blade, or the Flagg blade. Such blades have been subsequently improved by providing a curvature at the tip end to help lift the epiglottis. This later developed straight blade (1941) is commonly known as a Miller blade. Janeway designed a similar blade which gained only little popularity. More recently a Phillips U.S. Pat. No. 3,856,001 issue as an effort to further improve the straight blade laryngoscope. Another patented construction is described in U.S. Letters Pat. to Kandel No. 3,943,920.

PROBLEM

The foregoing noted straight blade laryngoscopes are similarly characteristic in that each is generally C shaped in cross section and which shape hinders the passage of the endotracheal tube. The lower part of the C shaped, cross section, which is referred to as the lower flange or lower edge, projects into the view of the anesthesiologist and acts as an obstruction to the passage of an endotracheal tube which is generally made of rubber or plastic; and which is curved. Also another problem noted with the "C" cross sectional shaped, straight blades is that the generally cylindrical shaped "C" section, being relatively large, obstructs visibility, since sighting is restricted to the tubular like tunnel defined by the "C" shaped section of the blade. Thus the "C" sectional shaped straight blade necessary to provide adequate visibility required a relatively large diameter. As a result, the relatively large diameter "C" shaped sections laryngoscope blades are relatively difficult to handle and frequently result in injury to the front teeth of a patient during a laryngoscope procedure because of the pressure required to be exerted thereon during the procedure.

OBJECTS

An object of this invention is to obviate the foregoing noted problems and to enhance the ease of laryngoscopy.

Another object is to provide a straight laryngoscope blade capable of attaining maximum visibility of the larynx and without obstructing the passage of the tube therethrough.

Another object is to provide a generally straight laryngoscope blade devoid of a lower inner flange so as to avoid obstruction to both the passage of a tube therethrough and the visibility to the larynx.

Another object is to provide a generally straight laryngoscope blade with a reduced overall height while increasing the exposure or viewing of the larynx.

Another object is to provide an improved laryngoscope of the straight blade type constructed so as to minimize pressure on a patient's teeth when in use.

BRIEF SUMMARY OF INVENTION

The foregoing objects and other features and advantages are attained by an improved laryngoscope blade of the straight blade type wherein the improvement resides in the cross-sectional shape of the blade which reduces the overall height of the blade while at the same time provides for maximum visibility of the larynx. This is attained by providing the straight portion of the blade with an arcuate cross-sectional shape which is less than "C" shape and which lower edge terminates in a laterally outwardly bent flange portion. The improved blade configuration enables the overall height of the blade to be reduced while at the same time obviates the objection heretofore encountered in intubation and visibility of the larynx. The free or tip end of the blade, which is inserted into a patient's mouth, is slightly curved to help lift the epiglottis.

FEATURES

A feature of this invention resides in the provision of an improved straight blade type laryngoscope having a arcuate cross-sectional shape along the straight portion thereof which is less than "C" shape in cross-section so as to eliminate the limited "tunnel vision" encountered with the conventionally known "straight type" laryngoscope blades, and which cross-sectional shape also obviates the obstruction to intubation of a tube into a patient's larynx.

Another feature resides in the provision of an improved laryngoxope blade of the straight type having a laterally outwardly bent flange so as to broaden the area of contact made with a patient's teeth, and thereby minimize any damage to such teeth during an endotracheal intubation procedure.

Other features and advantages will become more readily apparent to those skilled in the art when considered in view of the detailed description and drawings in which:

FIG. 1 is a side elevation view of a standard or known prior art construction of a straight type of laryngoscope blade.

FIG. 2 is a cross-section view of the blade of FIG. 1 illustrating its relationship to a patient's teeth when in use.

FIG. 3 is a side elevation view of a laryngoscope blade embodying the present invention drawn to essentially the same scale as the blade of FIG. 1.

FIG. 4 is a top plan view of the blade of FIG. 3.

FIG. 5 is a cross-sectional view of the blade of FIGS. 3 and 4 illustrating the relationship of said improved blade to a patient's teeth; drawn to the same scale as FIG. 2 and taken along line 5-5 on FIG. 3.

DETAILED DESCRIPTION

Figure 6:
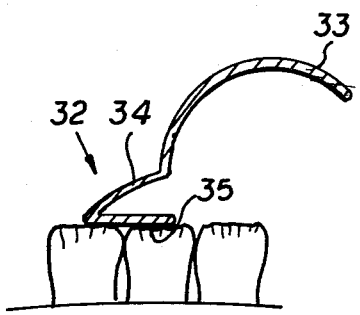
FIG. 6 is a cross-section shape of a modified blade construction embodying the present invention.

Referring to the drawings there is shown in FIGS. 1 and 2 a laryngoscope blade of a known construction; e.g., the straight type blade described in U.S. Pat. Nos. 2,433,705; 2,289,226, or 3,856,001. Such prior art blades 10 comprises essentially of tunnel shaped or "C" shape shaft portion 10A which is generally straight throughout, with the free or tip end 10B slightly curved. The usual light bulb 11 is located to one side of the blade 10 adjacent the tip end 10B. As best seen in FIG. 2, the lower edge portion 12 functions as a bearing point to rest on a patient's teeth during an endotracheal intubation procedure. The blades of the type shown also include a mounting means or hinge 13 (FIG. 8) whereby it can be readily attached to a handle portion (not shown) which generally contains the batteries for providing the electrical energy necessary to energize the light bulb 11. In order to provide sufficient visibility to the trachea, the diameter "D" of the blade 10 was made approximately 1.8 cm. As a result, experience has shown that such blades were difficult to manipulate in the mouth and further that the lower edge 12 imparted considerable pressure on a patient's teeth frequently causing the teeth to chip. Thus, the edge 12 defining essentially a line contact with the patient's teeth imparted considerable pressure thereon.

Figure 8:
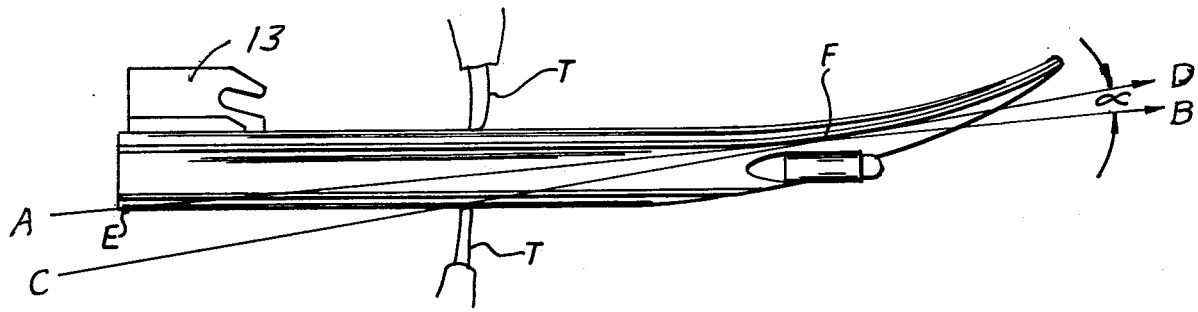
FIG. 8 is a side view of a conventional laryngoscope blade illustrating the limited line of vision occasioned thereby as compared to the line of vision occasioned by the improved blade of this invention.

Referring to FIG. 8, the "C" shaped cross-section of the shaft portion 10A, resulted in a restricted "tunnel vision" which was proportional to the diameter "D" of the shaft portion 10A. As seen in FIG. 8, the line of sight through such blade 10 was limited by the edge point E and a tangent point F as indicated by the sight line A-B. Thus with the known blade construction 10, the optimum line of sight was limited to a line of sight indicated by line A-B of a blade having an optimum diameter of D which has been generally determined to be approximately 1.8 cm.

Experience has further shown that the lower edge 12 of blade 10 also interfered with the passage of the tube during an intubation procedure.

Referring more specifically to FIGS. 3, 4 and 5, the foregoing noted problems have been obviated by an improved laryngoscope blade 20 which comprises an essentially straight shaft portion 20A which has an arcuate cross-section, as best seen in FIG. 5, which is less than "C" shape. The lower edge at 21 of the shaft 20A is laterally bent in an outward direction to define a lateral flange 22. Disposed to one side of the shaft portion 20A is the usual light bulb 23 to provide illumination. The free or tip end 20B is slightly curved to facilitate the lifting of the epiglottis. As best seen in FIG. 3, the terminal end portion along the X axis extends approximately 5 cms. and rises over said distance approximately 1 cm. along the Y axis. The mounting means (not shown) is provided on the other end of the shaft portion of attaching the blade 20 to a battery handle (not shown) as is well known.

With the construction described, the overall height portion H can be reduced from 1.8 cms. to between 1.5 cms. and 1.25 cms. without reducing the radius of the arcuate or cross-sectional portion of the shaft portion 20A. In other words, the radius of curvature of the shaft portion 20A of blade 20 is the same as the radius of optimum curvature of blade 10 while the overall height H is reduced from 1.8 cms. for the conventional blade 10 to 1.5 cms. for the present construction. Thus by the described construction of the present invention it will be apparent that the reduced height H greatly facilitates the manipulation of the blade 20 in a patient's mouth, while at the same time reducing the trauma to the patient's teeth as less pressure is required to be exerted on the teeth, and that pressure which may be occasioned is distributed over a greater surface area due to the lateral flange 22 as best seen in FIG. 5.

Referring to FIG. 8, it will be noted that the construction and shape of blade 20 further enhances the visibility of the trachea as the range of vision is indicated by line C-D. Because the lower edge 12 of the conventional "C" shape blade 10 is not present in the improved blade 20, the line of vision is not obstructed. Thus, with the blade 20, the line of vision extends from the patient's teeth indicated at T to the tangent point F. Thus the area of visibility of the trachea is increased by angle α. Also, the absence of the lower edge 12 in the improved described blade 20 obviates any obstruction heretofore encountered in the placement of a tube into a trachea.

Figure 7:
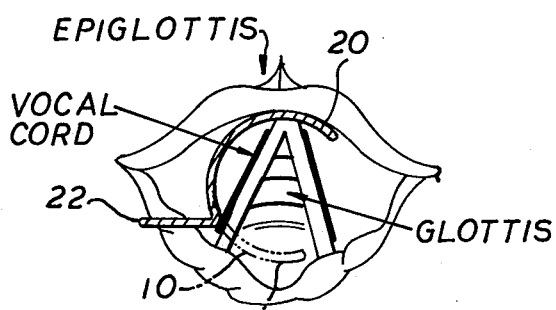
FIG. 7 is a view of the larynx as viewed by an anesthesiologist illustrating the comparative view of the larynx through a laryngoscope blade of the prior art construction of FIG. 1 (shown in dash lines) and the improved blade construction embodying the present invention (shown in solid lines).

Referring to FIG. 7, there is shown a view of the larynx as seen by an anesthesiologist. The dotted or dash line showing illustrates the location of a conventional straight blade 10 wherein it will be noted that the lower edge 12 obstructs the view and the passage of an endotracheal tube. Superimposed thereon, and shown in solid line, is the improved blade 20 described herein.

It will be noted that the overall height H of the improved blade is reduced making it easier to manipulate the blade while in the patient's mouth, while at the same time maintaining the same radius of curvature for the cross-sectional shape and enhancing the visibility of the trachea. Also, the lower edge 12 of the conventional blade 10 not being present in the improved blade 20 obviates the obstruction heretofore encountered in an intubation procedure. The laterally outwardly flared flange also functions to distribute any pressure imparted to the teeth over a greater area to thus reduce trauma and also help to keep the tongue out of the way.

FIG. 6 illustrates a modified cross-sectional shape for the improved blade construction 20 described herein. The blade modification of FIG. 6 is identical in all respects to that herein described except that the flange portion 32 there has been modified. As shown, the arcuate portion 33 of the shaft is outwardly bent at an angle thereto as indicated at 34, and which flange is then reversely bent to define a generally flat surface 35, which is adapted to rest on a patient's teeth during an intubation process. A blade 20 constructed with a flange 35, as shown by FIG. 6, when made of a resilient material has the further advantage that the V shaped flange 35 can function as a spring, which can permit the overall height H to be further reduced, if necessary. In all other respects the construction, function and operation of the blade illustrated by FIG. 6 is similar to that described with respect to FIGS. 3, 4 and 5.

While the present invention has been described with respect to several embodiments, it will be understood and appreciated that variations and modifications can be made without departing from the spirit and scope of the invention.

What is claimed is:

1. A laryngoscope blade comprising:
   an essentially straight portion having an end portion adapted to extend into the throat beneath the epiglottis,
   said straight portion being generally arcuate in cross section,
   a flange connected to one edge of said arcuate cross section,
   said flange being substantially co-extensive to a longitudinal edge of said straight portion,
   and said flange being turned laterally outwardly relative to the curvature of said arcuate cross section whereby the cross sectional arcuate curvature extends to one side of said flange,
   said flange extending laterally of said arcuate cross section an amount sufficient to rest on more than one tooth so as to distribute the pressure thereover, and said flange extending generally along an extension of a radius of said cross section.

2. The invention as defined in claim 1 wherein the cross section arcuate curvature extends approximately 1.5 cms. to one side of said flange.

3. The invention as defined in claim 1 wherein the arcuate cross section of said straight portion has a height in the range of approximately 1.25 cms to 1.5 cms.

4. The invention as defined in claim 3 wherein the width of said flange is approximately 0.8 cms.

5. The invention as defined in claim 4 wherein the free end of said straight portion is elevated along a curvilinear line.

6. The invention as defined in claim 5 wherein said free end is elevated approximately 1 cm.

7. The invention as defined in claim 6 wherein said 1 cm. elevation occurs in the end 5 cms. of length of said blade.

8. The invention as defined in claim 1 wherein said flange is reversely bent.

9. A laryngoscope blade comprising:
   an essentially straight blade portion having an arcuate cross section which is adapted to extend into the throat with the inner end disposed beneath the epiglottis,
   said arcuate cross section terminating in spaced longitudinal edges,
   a flange extending along one of said longitudinal edges,
   said flange being disposed laterally outwardly and to one side of said longitudinal edge,
   and said flange being reversely bent to define an acute angle at the juncture of said bend,
   and said reversely bent portion defining a flat for engaging the teeth.

10. A laryngoscope blade as defined in claim 1 wherein said arcuate cross section of said straight portion is less than 180°.

* * * * *